(12) United States Patent
Doerr et al.

(10) Patent No.: US 8,774,919 B2
(45) Date of Patent: Jul. 8, 2014

(54) IMPLANTABLE CARDIAC THERAPY DEVICE

(75) Inventors: Thomas Doerr, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/602,321

(22) Filed: Sep. 4, 2012

(65) Prior Publication Data

US 2013/0066142 A1  Mar. 14, 2013

Related U.S. Application Data

(60) Provisional application No. 61/534,392, filed on Sep. 14, 2011.

(51) Int. Cl.
| | |
|---|---|
| *A61M 1/12* | (2006.01) |
| *A61N 1/39* | (2006.01) |
| *A61M 1/10* | (2006.01) |
| *A61N 1/362* | (2006.01) |
| *A61N 1/365* | (2006.01) |

(52) U.S. Cl.
CPC ..... *A61M 1/1086* (2013.01); *A61M 2205/3331* (2013.01); *A61M 1/10* (2013.01); *A61N 1/3627* (2013.01); *A61N 1/36521* (2013.01); *A61M 2230/65* (2013.01); *A61N 1/3956* (2013.01); *A61M 1/122* (2013.01)
USPC .......................................................... 607/16

(58) Field of Classification Search
CPC ....... A61M 1/1086; A61M 1/10; A61M 1/22; A61M 2205/3331; A61M 2205/3334; A61M 2230/04; A61M 2230/06; A61M 2230/65; A61N 1/3956; A61N 1/3627; A61N 1/36521
USPC ...................... 600/16–17; 607/17, 22, 24, 5–6
See application file for complete search history.

(56) References Cited

U.S. PATENT DOCUMENTS

| | | | | |
|---|---|---|---|---|
| 4,467,807 | A | * | 8/1984 | Bornzin ........................ 607/22 |
| 5,800,467 | A | * | 9/1998 | Park et al. .................... 607/17 |
| 6,179,773 | B1 | * | 1/2001 | Prem et al. .................... 600/17 |
| 6,438,421 | B1 | * | 8/2002 | Stahmann et al. ............. 607/9 |
| 2003/0074144 | A1 | | 4/2003 | Freed et al. | |

FOREIGN PATENT DOCUMENTS

| | | |
|---|---|---|
| WO | 2006/020942 | 4/2003 |
| WO | 2006/122036 | 11/2006 |
| WO | 2010/030904 | 8/2010 |

OTHER PUBLICATIONS

European Search Report, dated Nov. 23, 2012, 4 pages.

* cited by examiner

*Primary Examiner* — Mark W Bockelman
(74) *Attorney, Agent, or Firm* — ARC IP Law, PC; Joseph J. Mayo

(57) ABSTRACT

A cardiac therapy device having a cardiac assist pump, a defibrillation unit, and a control unit, which is connected to the cardiac assist pump and the defibrillation unit to control them. The cardiac assist pump is implemented in case of use to pump blood from a ventricle into an associated artery and thus relieve the respective ventricle. The defibrillation unit is implemented for automatic defibrillation of a ventricular fibrillation and the control unit is implemented to activate the cardiac assist pump and the defibrillation unit in a coordinated manner in case of a ventricular fibrillation such that the cardiac assist pump first increases its performance to initially cause a pressure relief of at least one assisted ventricle in case of use and the defibrillation unit only subsequently delivers a defibrillation shock, when a ventricular pressure relief is provided.

12 Claims, 4 Drawing Sheets

IMPLANTABLE CARDIAC THERAPY DEVICE

This application claims the benefit of U.S. Provisional Patent Application 61/534,392 filed on 14 Sep. 2011, the specification of which is hereby incorporated herein by reference.

BACKGROUND OF THE INVENTION

1. Field of the Invention

At least one embodiment of the invention relates to an implantable cardiac therapy device.

2. Description of the Related Art

Known implantable cardiac therapy devices include, for example, cardiac assist pumps, which are connected to a ventricle of a heart and an associated artery (pulmonary artery or aorta) and are implemented to pump blood from a respective ventricle in an assisting manner into a respective associated artery (pulmonary artery, aorta) and thus relieve the respective ventricle.

Other known implantable cardiac therapy devices include cardiac stimulators such as cardiac pacemakers or defibrillators/cardioverters having a defibrillation unit for the automatic defibrillation of a ventricular fibrillation.

Supplying a patient with multiple such devices is also known.

BRIEF SUMMARY OF THE INVENTION

Disclosed is a combination therapy device for increasing the defibrillation therapy efficiency in patients having very strongly restricted ventricular pumping function, which represents a combination of an implantable cardioverter/defibrillator (ICD) and a ventricular assist pump (ventricular assist device, VAD)—referred to here as a cardiac assist pump—and has a control unit which is connected in a controlling manner to the cardiac assist pump and the defibrillation unit and is implemented, in the case of a ventricular fibrillation, to activate the cardiac assist pump and the defibrillation unit in a coordinated manner such that the cardiac assist pump initially increases its performance to initially cause a pressure relief of at least one assisted ventricle in case of use and the defibrillation only subsequently delivers a defibrillation shock, when a ventricular pressure relief is provided.

The control unit therefore forms a therapy coordination unit, which first increases the performance of the assist pump in the case of a ventricular fibrillation in such a manner that initially a pressure relief of the supported ventricle or ventricles occurs and only then is an electrical defibrillation triggered, when the ventricular pressure relief is provided.

Also disclosed is the finding that in patients having very strongly restricted ventricular pumping function, there is a significantly increased risk of ventricular fibrillation (VF). At the same time, in particular in these patients, the therapy efficiency of solely electrical defibrillation is restricted. The reason for this is the triggering mechanism for VF in these patients: the spontaneously occurring VF results in additional filling of the heart, which is no longer pumping, through the venous backflow, and therefore an increase of the wall tension of the myocardium.

This elevated wall tension is in turn the cause of intrinsic fibrillation, i.e., without prior reduction of the wall tension/ventricle filling, electrical defibrillation remains ineffective.

In addition, a myocardial ischemia occurring in the above-mentioned patients also causes worsening of the defibrillation prognosis.

The mentioned patients frequently fulfill the indication for a ventricular assist pump (VAD), since in these patients the degree of the compensation is sufficiently advanced that adequate oxygen supply of the systemic circulation and myocardial perfusion is no longer provided. These VAD systems are currently designed solely as pump systems and are not capable of treating a spontaneous VF. Since the pump function also maintains a circulation during a VF, these patients can be externally defibrillated, if emergency medical care is provided rapidly enough. The described implantable cardiac therapy device accordingly has the effect of significantly increasing the therapy efficiency of an automatic electrical defibrillation in patients having very strongly restricted pumping function.

The implantable cardiac therapy device preferably has a pressure sensor, e.g., as a component of the cardiac assist pump, which is connected to the control unit. The control unit may then be implemented so that it performs the control of the pressure relief before defibrillation based on the output signal of the pressure sensor.

The defibrillation unit is preferably connected to at least one defibrillation electrode, which is designed to deliver a defibrillation shock, and which is a component of the cardiac assist pump or a fluid connection of the cardiac assist pump. The defibrillation electrodes are therefore integral components of the assist pump.

In addition, the implantable cardiac therapy device can have an oxygen sensor, which is connected to the control unit and, in operation, delivers an output signal that indicates the blood oxygen content. The control unit is preferably implemented so that it additionally controls a defibrillation shock delivery based on the output signal of the myocardial oxygen sensor.

Moreover, the implantable cardiac therapy device can have a programmable timer, which is connected to the control unit or is a component thereof. The control unit is preferably implemented so that it additionally controls the control of the defibrillation shock delivery with the aid of the programmable timer, so that a defined runtime of the assist pump having increased performance is ensured before the defibrillation.

According to a further preferred embodiment variant, the implantable cardiac therapy device additionally comprises a stimulation unit for post-shock stimulation, which is connected to the control unit and is implemented to supply electrical stimulation pulses for stimulating a ventricular contraction as needed, controlled by the control unit.

The implantable cardiac therapy device, as a combination therapy device, can also have a cardiac stimulator or at least one stimulation unit which is controlled by the control unit, which is optionally implemented in combination with the control unit for the purpose of stimulating both ventricles of a heart in terms of a cardiac resynchronization therapy (CRT).

The implantable cardiac therapy device preferably has an impedance sensor for detecting an intracardiac impedance and a cardiac stimulator or at least one stimulation unit, controlled by the control unit, which are connected to the control unit. The control unit can be implemented to control a delivery of stimulation pulses as a function of an output signal of the impedance sensor, which indicates an intracardiac impedance. In particular, the control unit can be implemented, in connection with the impedance sensor and the stimulation unit, for the purpose of controlling the stimulation on the basis of an output signal of the impedance sensor, which indicates a cardiac contractility, in such a manner that an increase of the contractility which meets the demands results. In this way, a combination therapy device having a CCM stimulator (cardiac contractility modulation) results, to increase the contractility to meet the demands.

In addition, the implantable cardiac therapy device can have means for detecting and analyzing rhythmological information and the control unit can be implemented to control the cardiac assist pump on the basis of rhythmological information such that the cardiac assist pump relieves a heart to meet the demands. The means for detecting and analyzing rhythmological information preferably comprise one or more sensing units, which are connected to the control unit, the means for detecting and analyzing rhythmological information being implemented to recognize and differentiate ventricular arrhythmias such as ventricular fibrillations and ventricular tachycardias. The means for detecting and analyzing rhythmological information can be implemented in this case, for example, by a correspondingly implemented control unit and the sensing units connected thereto. The detection and analysis of rhythmological information can be performed, for example, based on algorithms or criteria known per se, such as the SMART algorithm, morphology criteria, etc.

In addition, any combination of monoventricular and biventricular cardiac assist pumps (VAD pumps) with known systems for cardiac electrotherapy may be utilized with embodiments of the invention.

Furthermore a method for treating cardiac insufficiency is disclosed, comprising the steps of operating a cardiac assist pump, providing a defibrillation unit, providing a control unit, wherein the cardiac assist pump and the defibrillation unit are connected to and controlled by the control unit, and—and in case of ventricular fibrillations activating the ventricular assist pump and the defibrillation unit in a coordinated manner, such that the cardiac assist pump first increases its performance to initially cause a pressure relief of at least one assisted ventricle, and the defibrillation unit only subsequently delivers a defibrillation shock, when a ventricular pressure relief is provided.

The method can be exploited with the cardiac therapy devices described above, especially it can benefit from the different embodiments described above.

BRIEF DESCRIPTION OF THE DRAWINGS

The invention will be explained in greater detail on the basis of exemplary embodiments with reference to the figures. In the figures.

DETAILED DESCRIPTION OF THE INVENTION

Figure 1:
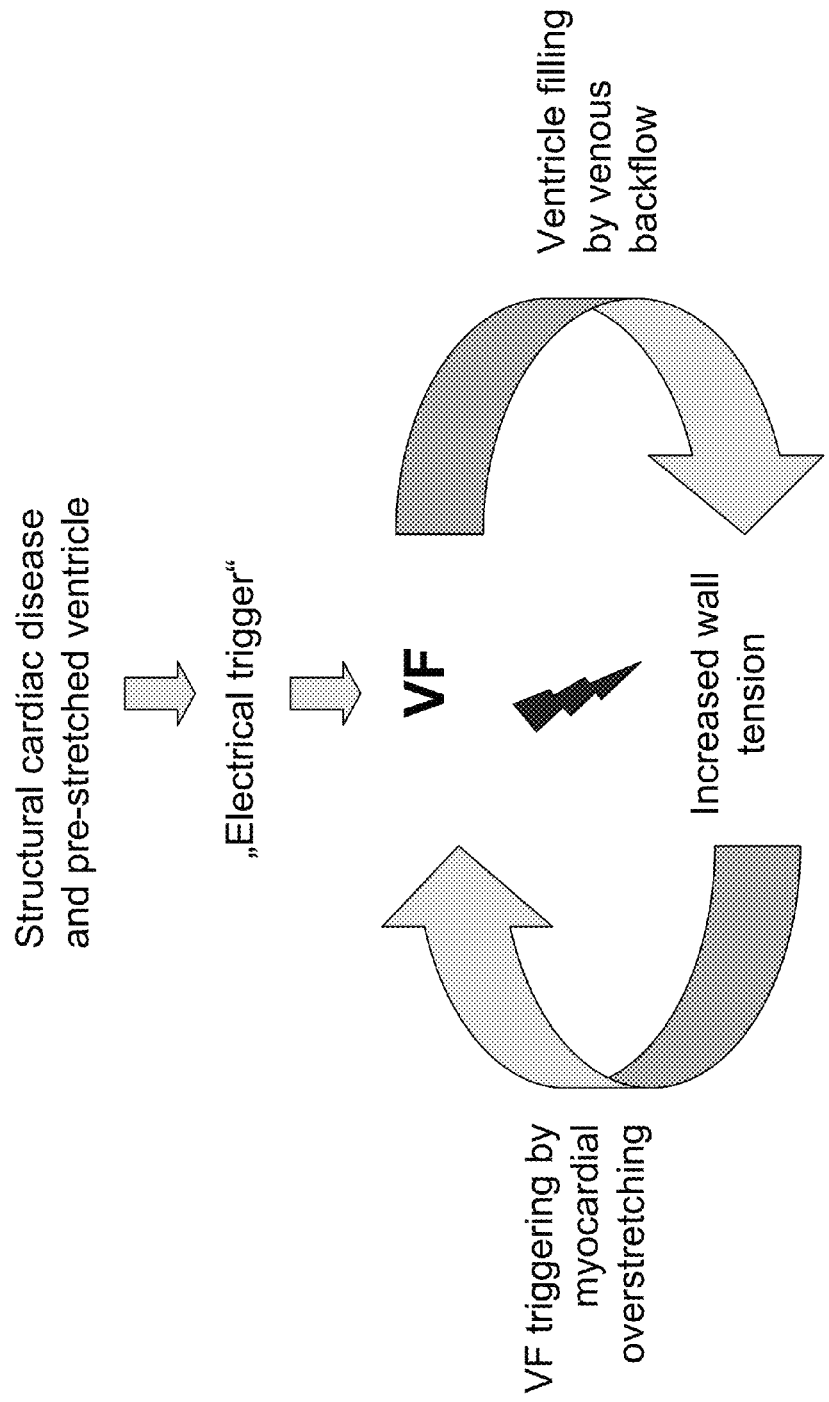
FIG. 1: shows an illustration of the clinical problems of patients having strongly pronounced cardiac insufficiency.

The clinical problem of the patients having strongly pronounced cardiac insufficiency is shown in FIG. 1. These patients suffer from pronounced structural cardiac disease, accompanied by strongly expanded left/right ventricle(s) because of elevated pressure conditions. These conditions significantly increase the vulnerability to an electrical trigger for triggering a spontaneous ventricular fibrillation. For this reason, these patients are also supplied with an implanted defibrillator (typically in combination with a resynchronization stimulator CRT-D).

However, the therapy efficiency of electrical defibrillation is limited in these patients, since there is no longer a pumping function of the heart in the case of ventricular fibrillation, but the venous backflow significantly increases the blood volume in the heart. An increased ventricular wall tension thus occurs, which in turn represents a further trigger mechanism for a VF. Since the electrical defibrillation can only "reset" the electrical activity of the VF, but cannot resolve the wall tension, the patient remains in a therapy-resistant ventricular fibrillation.

For this reason, defibrillation testing is frequently dispensed with in the case of patients having severe cardiac insufficiency during the CRT-D implantation.

Figure 2:
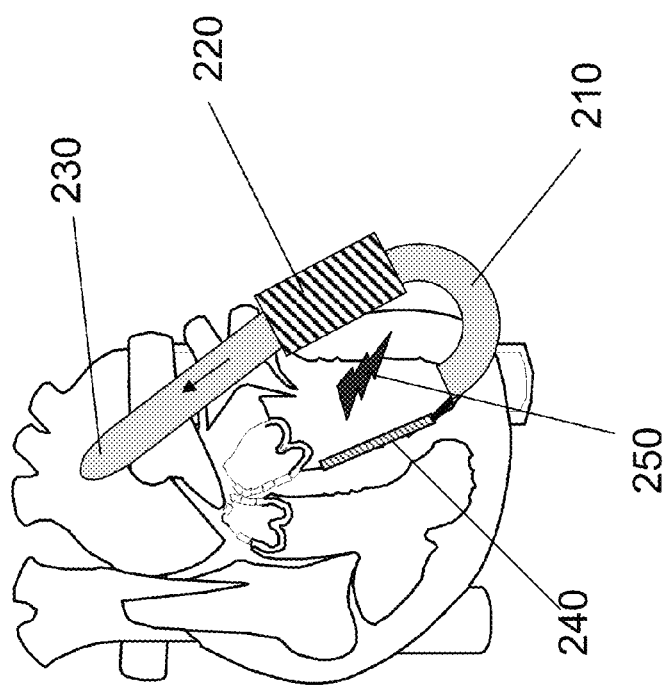
FIG. 2: shows an implantable cardiac therapy device according to an embodiment of the invention as a combination device made of cardiac assist pump and defibrillator.

The overall system according to an embodiment of the invention is shown in an exemplary embodiment in FIG. 2. A supply line (210) is implanted in the left ventricle of the patient to connect the assist pump (220). This supply line has the object of causing a part of the blood to flow from the left ventricle to the pump (220). The assist pump in turn pumps the blood volume into the aorta (230) and thus relieves the left ventricle. In addition, the system according to an embodiment of the invention has a defibrillation and sensing electrode (240) in the left ventricle.

Since the patient is anticoagulated by the assist pump in any case, the implantation of a left-ventricular electrode is noncritical. In this configuration, the pump housing of the assist pump (220) is used as the counter electrode and defibrillation generator, i.e., the defibrillation shock (250) (shown as a dark jagged bolt) is delivered between pump housing (220) and left-ventricular shock electrode (240).

Figure 3:
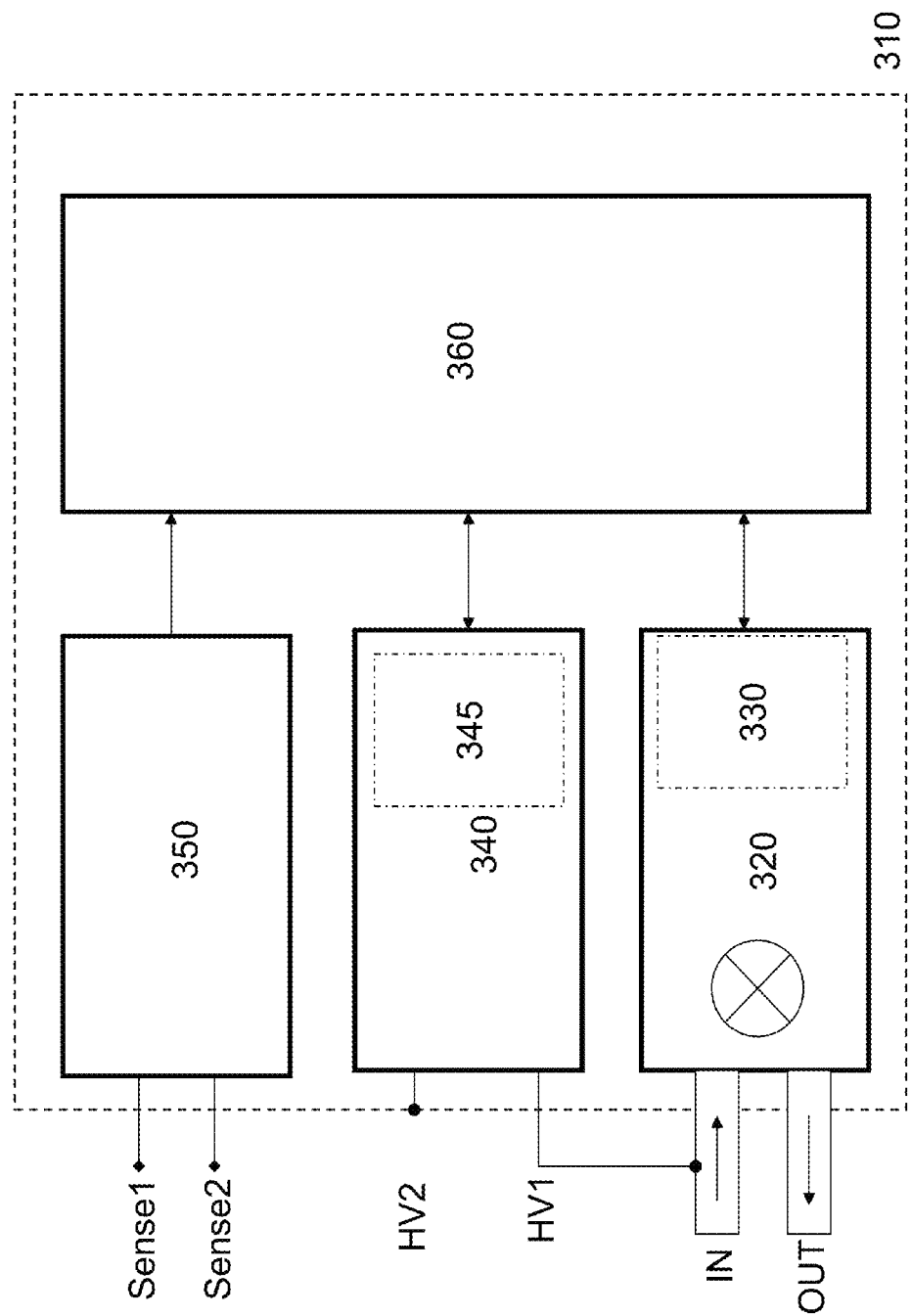
FIG. 3: shows a block diagram of the combination therapy device from FIG. 2.

The block diagram of the implantable cardiac therapy device (310) is shown in the form of a combination therapy device in FIG. 3. The actual pump (320), which is typically controlled via a pressure sensor system (330) having a pressure sensor, is located inside the VAD pump housing (i.e., the housing of the cardiac assist pump). This pump (320) is connected to the ventricular inflow (IN) and aortal outflow (OUT). In addition, the device comprises a defibrillator or a defibrillation unit (340) for delivering defibrillation shocks similarly to an ICD. This defibrillation unit (340) is connected to a ventricular shock electrode (HV1) as the defibrillation electrode. This can be a separate shock coil or an integral component of the ventricular inflow line (IN). The counter electrode (HV2) is formed by an electrically conductive housing of the implantable cardiac therapy device (310).

An impedance measurement unit (345) is indicated, which forms an impedance sensor for detecting an intracardiac impedance in connection with the shock electrodes (HV1 and HV2). The intracardiac impedance is a function of, inter alia, the blood volume in the ventricle at a respective point in time, so that the time curve of the intracardiac impedance reflects the contraction movements of the ventricle. Thus, parameters which describe the contractility of the ventricle and—in the context of the closed-loop stimulation—the hemodynamic demand of a patient can be derived from an output signal originating from the impedance sensor in a way known per se, which are then analyzed by the control unit (360) as the therapy control unit to control the cardiac assist pump (320) and the defibrillation unit (340).

Furthermore, a rhythm sensing unit (350) is installed in the therapy device, which senses and classifies the ventricular cardiac rhythm, typically via a bipolar electrode (Sense1, 2). The coordination of the combined therapy functions is assumed by the therapy control unit (360), which assumes the coordination of the pumping and defibrillation therapy according to FIG. 4.

Figure 4:
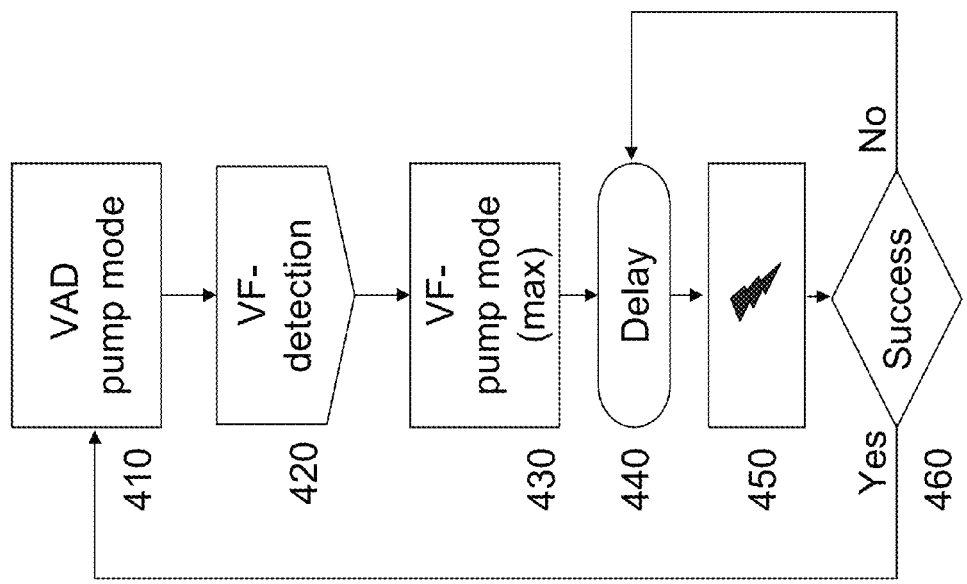
FIG. 4: shows an exemplary flowchart for the control of the combination therapy.

A possible flowchart for the control of the combination therapy is shown in FIG. 4. The system is normally in the state

410: VAD pump mode. In this state (410), a part of the required cardiac output per minute is pumped by the VAD pump from the left ventricle into the aorta.

If a ventricular fibrillation is classified (420) by the detection unit, the therapy control unit switches the pump mode to a higher performance (430), in order to thus significantly relieve the ventricle from the volume strain of the venous backflow. After a programmable time or delay (440) or alternatively the detection of suitable pressure conditions using the pressure sensor intrinsic to the VAD, a first defibrillation attempt (450) is performed. Subsequently, as a function of the defibrillation success (460), the normal VAD pump mode (410) is activated or a further defibrillation attempt by the optionally modified VF pump mode is prepared, otherwise processing continues at (440) which implements the programmable time or delay, or alternate pressure detection described above.

At least one embodiment of the invention offers the advantage of significantly increasing the electrical defibrillation efficiency and therefore the therapy efficiency in patients having strongly restricted pumping function.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable cardiac therapy device having
    a cardiac assist pump, which is configured to connect to a respective ventricle of a heart and a respective associated artery and when activated, is configured to pump blood from the respective ventricle into the respective associated artery and thus assist or relieve the respective ventricle;
    a defibrillation unit configured to deliver a defibrillation shock in response to a ventricular fibrillation;
    a control unit, which is connected to the cardiac assist pump and the defibrillation unit, wherein said control unit is configured to control the cardiac assist pump and the defibrillation unit and, in case of said ventricular fibrillation, to
        activate the cardiac assist pump and the defibrillation unit in a coordinated manner such that
            the cardiac assist pump first increases performance to initially provide a pressure relief of the respective ventricle, and
            the defibrillation unit only subsequently delivers said defibrillation shock, when the pressure relief of the respective ventricle is provided;
    a pressure sensor which indicates a ventricular internal pressure and provides an output signal, wherein the control unit is connected to the pressure sensor, wherein the pressure sensor is located inside the cardiac assist pump, and wherein the pressure sensor is configured to detect a pressure in the respective ventricle and wherein the control unit is configured to control either the defibrillation unit or the cardiac assist pump or both, as a function of the output signal of the pressure sensor; and,
    a programmable timer, which is connected to the control unit or is a component thereof, wherein the control unit is configured to additionally control the delivery of the defibrillation shock through use of the programmable timer so that a defined runtime of the cardiac assist pump with increased performance is ensured before delivery of the defibrillation shock occurs.

2. The implantable cardiac therapy device according to claim 1, further comprising at least one defibrillation electrode wherein the defibrillation unit is connected to the at least one defibrillation electrode, and wherein the at least one defibrillation electrode is a component of the cardiac assist pump or a fluid connection portion of the cardiac assist pump.

3. The implantable cardiac therapy device according to claim 1, further comprising an oxygen sensor, which is connected to the control unit and provides an output signal that indicates the blood oxygen content in operation, wherein the control unit is additionally configured to control delivery of the defibrillation shock based on the output signal of the oxygen sensor.

4. The implantable cardiac therapy device according to claim 1, further comprising a stimulation unit that is configured for post-shock stimulation, wherein the stimulation unit is connected to the control unit and is controlled by the control unit, to provide electrical stimulation pulses to stimulate a ventricular contraction.

5. The implantable cardiac therapy device according to claim 1, further comprising a cardiac stimulator or at least one stimulation unit controlled by the control unit, and which is configured to optionally in combination with the control unit, stimulate both ventricles of the heart to achieve cardiac resynchronization therapy.

6. The implantable cardiac therapy device according to claim 1, further comprising an impedance sensor configured to detect an intracardiac impedance and provide an output signal and a cardiac stimulator or at least one stimulation unit controlled by the control unit, which is connected to the control unit, wherein the control unit is configured to control delivery of stimulation pulses as a function of the output signal of the impedance sensor.

7. The implantable cardiac therapy device according to claim 6, wherein the control unit is configured in connection with the impedance sensor and the at least one stimulation unit, to control stimulation based on the output signal of the impedance sensor, which indicates a cardiac contractility, to increase the cardiac contractility to meet demand.

8. The implantable cardiac therapy device according to claim 1, further comprising a unit configured to detect and analyze rhythmological information wherein and wherein the control unit is configured to control the cardiac assist pump based on the rhythmological information so that the cardiac assist pump relieves the heart to meet demand.

9. The implantable cardiac therapy device according to claim 8, wherein the unit to detect and analyze the rhythmological information comprises one or more sensing units, which are connected to the control unit, wherein the unit to detect and analyze the rhythmological information is configured to recognize and differentiate ventricular arrhythmias including ventricular fibrillations and ventricular tachycardias.

10. The implantable cardiac therapy device according to claim 1, wherein the cardiac assist pump comprises a pressure sensor system, and wherein the pressure sensor system includes the pressure sensor.

11. The implantable cardiac therapy device according to claim 1, wherein the pressure sensor is further configured to output a suitable pressure condition, such that the cardiac assist pump is further configured to first increase performance after a programmable time or delay, or after a detection of the suitable pressure condition.

12. A method for treating cardiac insufficiency with an implantable cardiac therapy device comprising:

pumping blood, when activated, from a respective ventricle into a respective associated artery of a heart to assist or relieve the respective ventricle with a cardiac assist pump configured to connect to the respective ventricle of the heart and the respective associated artery;

delivering a shock with a defibrillation unit in response to a ventricular fibrillation;

indicating a ventricular internal pressure and providing an output signal with a pressure sensor located inside the cardiac assist pump; wherein the pressure sensor is configured to detect a pressure in the respective ventricle;

controlling the cardiac assist pump and the defibrillation unit with a control unit, which is connected to the cardiac assist pump, the pressure sensor and the defibrillation unit, wherein said control unit is configured in case of said ventricular fibrillation by activating the cardiac assist pump and the defibrillation unit in a coordinated manner and increasing performance of the cardiac assist pump first to initially provide a pressure relief of the respective ventricle, and delivering said defibrillation shock via the defibrillation unit to only subsequently deliver said defibrillation shock when the pressure relief of the respective ventricle is provided; and controlling either the defibrillation unit or the cardiac assist pump or both, as a function of the output signal of the pressure sensor; and, controlling the delivery of said defibrillation shock through the use of a programmable timer so that a defined runtime of the cardiac assist pump with increased performance is ensured before delivery of the defibrillation shock occurs, wherein the programmer timer is connected to the control unit or is a component thereof.

* * * * *